(12) United States Patent
Farhi

(10) Patent No.: US 7,001,364 B1
(45) Date of Patent: Feb. 21, 2006

(54) NEEDLE SAFETY CAP DEVICE

(76) Inventor: Parham Farhi, 777 W. Germantown Pike, Apt. 815, Plymouth Meeting, PA (US) 19462

( * ) Notice: Subject to any disclaimer, the term of this patent is extended or adjusted under 35 U.S.C. 154(b) by 117 days.

(21) Appl. No.: 10/639,328

(22) Filed: Aug. 12, 2003

Related U.S. Application Data

(60) Provisional application No. 60/403,252, filed on Aug. 13, 2002.

(51) Int. Cl.
  *A61M 5/32* (2006.01)
  *A61M 5/00* (2006.01)
(52) U.S. Cl. ................................. 604/198; 604/110
(58) Field of Classification Search ............... 604/110, 604/192, 198, 263, 187, 197, 218; 128/919
  See application file for complete search history.

(56) References Cited

U.S. PATENT DOCUMENTS

| | | | |
|---|---|---|---|
| 4,731,059 A * | 3/1988 | Wanderer et al. ........... 604/192 |
| 5,069,669 A | 12/1991 | Kole |
| 5,147,303 A * | 9/1992 | Martin ........................ 604/110 |
| 5,163,918 A * | 11/1992 | Righi et al. ................. 604/198 |
| 5,250,031 A | 10/1993 | Kaplan |
| 5,295,972 A | 3/1994 | Mischenko |
| 5,356,387 A | 10/1994 | Sirbola |
| 5,385,550 A * | 1/1995 | Su et al. ..................... 604/110 |
| 5,411,492 A | 5/1995 | Sturman |
| 5,415,645 A * | 5/1995 | Friend et al. ................ 604/110 |
| 5,630,803 A | 5/1997 | Tamaro |
| 5,964,731 A | 10/1999 | Kovelman |
| 6,015,397 A | 1/2000 | Elson |
| 6,077,253 A * | 6/2000 | Cosme ........................ 604/263 |
| 6,093,170 A * | 7/2000 | Hsu et al. .................... 604/110 |
| 6,183,445 B1 * | 2/2001 | Lund et al. .................. 604/198 |
| 6,319,233 B1 * | 11/2001 | Jansen et al. ................ 604/192 |
| 6,471,677 B1 * | 10/2002 | Domici, Jr. .................. 604/198 |

\* cited by examiner

*Primary Examiner*—Manuel Mendez
*Assistant Examiner*—Mark K. Han

(57) ABSTRACT

This invention is a device for shielding a needle to prevent accidental needle sticks. The device contains two shields that surround the needle (cap the needle), one of which attaches to the needle hub, and the second which extends beyond the tip of the needle. The second shield slides into the first shield thereby exposing the needle during injection. The device also contains a spring that holds the second shield in the extended position except when compressed, and a locking mechanism that secures the second shield automatically after injection in the extended position except when unlocked by the user prior to injection. The spring ensures that the second shield remains in the extended position when mechanism is unlocked, shielding the needle, except when the spring is compressed by pressure against the injection site, and when the needle is withdrawn from the injection site, the second shield is pushed back and automatically locked into place for disposal of the needle.

7 Claims, 6 Drawing Sheets

NEEDLE SAFETY CAP DEVICE

CROSS-REFERENCE TO RELATED APPLICATIONS

This application claims the benefit of 60/403,252 PPA registration No. 50,314, filed Aug. 13, 2002 by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention relates to a device for needle safety, specifically to a device to protect from injury due to accidental needle sticks.

2. Discussion of Prior Art

Needle stick injuries are one of the most common job related injuries among health care workers, and may result in transmission of blood-born pathogens. The risk is greater due to the increasing prevalence of serious infectious diseases in the general population such as Hepatitis B, Hepatitis C, and HIV. Needle stick injuries can occur during use of a range of medical devices, including hypodermic syringes, blood collection needle sets ("butterfly syringes"), intravenous catheters, and other intravenous infusion equipment.

More than 8 million health care workers in the United States work in hospitals and other health care settings. Estimates indicate that 600,000 to 800,000 needle stick and other percutaneous injuries among health care workers occur annually. Percutaneous injury (e.g., needle stick) was associated with 89% of the documented transmissions of HIV to healthcare workers between 1985 and 1999. Approximately 38% of percutaneous injuries occur during use of a sharp device and 42% occur after use and before disposal.[1]

There is an ongoing need for a safe and effective needle cap device because it has the potential to save lives. This need has been recognized, and has since become a law. Congress passed the Needle Stick Safety and Prevention Act directing OSHA to revise the blood-borne pathogens standard. This revision established in greater detail the requirement that employers identify and make use of effective and safer medical devices. The OSHA revision was published on Jan. 18, 2001, and became effective on Apr. 18, 2001.

Directives relating to safety devices to prevent needle sticks published by the National Institute for Occupational Safety and Health include the following desirable characteristics:

1. The safety feature is an integral part of the device.
2. The device preferably works passively (i.e., it requires no activation by the user).
3. The user can easily tell whether the safety feature is activated.
4. The safety feature remains protective through disposal.
5. The device performs reliably.
6. The device is easy to use and practical.
7. The device is safe and effective for patient care[1].

There are more than 100 products to reduce the risk of accidental needle sticks currently on the market, (U.S. Pat. No. 5,630,803, U.S. Pat. No. 6,015,397, U.S. Pat. No. 5,069,669, U.S. Pat. No. 5,295,972, U.S. Pat. No. 5,250,031, U.S. Pat. No. 5,411,492, U.S. Pat. No. 5,407,070, U.S. Pat. No. 5,385,550, U.S. Pat. No. 5,356,387, and U.S. Pat. No. 5,964,731 for example) but studies have shown that the users are dissatisfied with currently available needle safety devices, and in some cases that the incidence of accidental needle sticks rises with the use of these safety needles[2]. Recapping of needles, although prohibited by policy in many workplaces, is a major reason for needle stick injuries.

The needle safety devices fall into two categories of action; active and passive. The majority of devices use the active mechanism. Active devices require the health care worker to activate the safety mechanism. Failure to activate leaves the worker unprotected. Proper use by the health care worker is the primary factor in the effectiveness of these devices.

Several types of active needle safety devices have been proposed. Since these devices rely on the worker for activation of the safety mechanism there is a chance that the worker will be left unprotected. Some of these devices require the worker to place his/her fingers in front of the needle which can be a safety hazard.

Very few needle safety devices utilize passive activation. Passive safety devices do not need to be activated by the health care worker. They remain in effect before, during, and after use. Passive devices enhance the safety design and are more likely to have a greater impact on prevention than active devices.

There are a few passive needle safety devices that have been proposed. These devices are very complex with many parts, and most cannot be used with standard injection devices. This means that they are expensive to manufacture. Also, in many cases, the user will also have to modify their injection technique.

All of the needle safety devices suffer from a number of disadvantages:

(a) Most devices utilize an active system to activate the safety mechanism. The safety mechanism is not automatically in effect. If the worker fails to activate the system or activates the system incorrectly, the safety mechanism will not be in effect and the worker will be left unprotected.

(b) Most devices have many complex parts, which are difficult and expensive to manufacture.

(c) Most devices modify the entire syringe. This is very costly to manufacture, and it may result in a modification of injection technique.

(d) Most devices are non-compatible with other types of injection devices.

(e) Most devices cannot be unlocked for reuse.

(f) The devices do not meet all of OSHA and FDA suggested criteria for needle safety devices:

1) The safety feature is not an integral part of the device.

2) The devices do not work passively.

3) The user cannot easily tell whether the safety feature is activated.

4) The safety feature does not remain protective through disposal.

5) The device is not easy to use and not always practical.

6) The device is not always safe and effective for patient care.

BACKGROUND OF INVENTION—OBJECTS AND ADVANTAGES

It is an object of this invention to have a needle safety device for shielding a needle to prevent accidental needle sticks and the accompanying risk of transmission of blood-born pathogens such as HIV and Hepatitis. Accordingly, several objects and advantages of the present invention are:
- (a) to provide a needle safety cap device such that the device works passively and requires no activation by the user to perform the shielding function.
- (b) to provide a needle safety cap device that uses a simple and proven technology for the locking mechanism that is inexpensive to manufacture.
- (c) to provide a needle safety cap device that does not modify the syringe.
- (d) to provide a needle safety cap device which is compatible with all needle injection devices.
- (e) to provide a needle safety cap device that can be unlocked for additional injections.
- (f) to provide a needle safety cap device that meets all of the OSHA and FDA criteria including:
  1) the safety feature is an integral part of the needle assembly and need not be installed in the workplace to be protective before and after use of the needle.
  2) the device works passively.
  3) the user can easily tell if the safety feature is activated.
  4) the safety feature remains protective through disposal.
  5) the device is easy to use and practical.
  6) the device is always safe and effective for patient care.

It is an object of this invention to have a needle safety cap device for shielding a needle in such a way that the device is locked in place and must be unlocked in order for the shield to retract when making an injection. It is a further object of this invention to have such a needle safety cap device that can be installed onto the hub portion of the needle to a medical device such as a syringe or catheter. It is a further object of this invention to have a needle safety cap device comprising two shields, the second of which can only retract into the first to expose the needle when the device is unlocked and an injection is being performed and which automatically springs out of the first and locks into place to shield the needle when the injection is complete, and remains locked during disposal of the needle.

It is also an object of this invention to have a needle safety cap device which can be manually unlocked if another injection is needed. It is also an object of this invention to have a needle safely device that indicates when the locking mechanism is in effect. It is further an object of this invention to have a needle safety cap device that has a locking mechanism that is incorporated directly into the cap which dos not modify the whole injection device.

Further objects and advantages of my invention will become apparent from a consideration of the drawings and ensuing description.

SUMMARY

In accordance with the present invention a needle safety device comprises a locking mechanism incorporated into the cap, which consists of two shields and a spring, for use in combination with a portion connected to the needle hub.

DRAWINGS—FIGURES

Figure 6A:
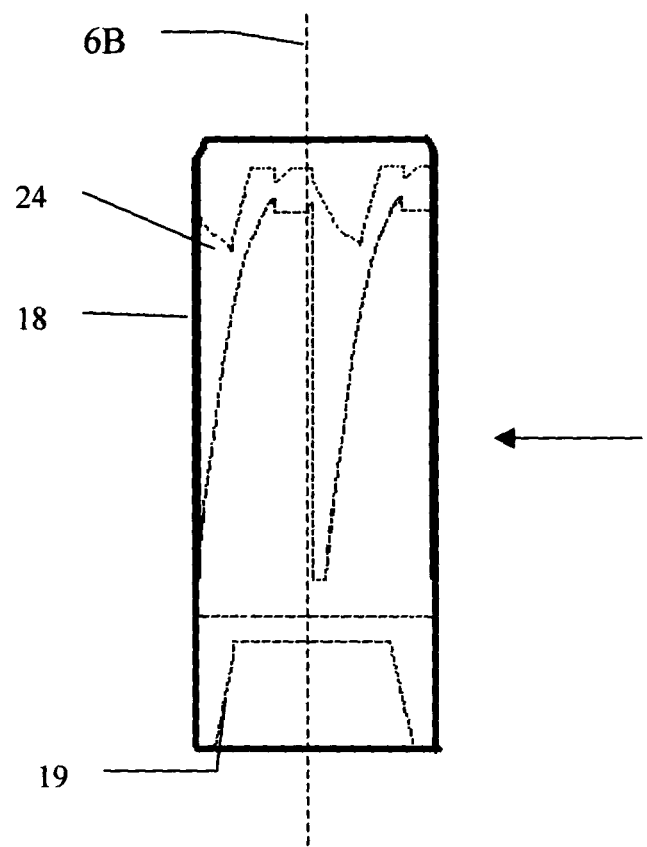

FIG. 6A shows another view of the first shield portion of the needle safety cap device along with its internal structure. The dotted line shows the plane in which sectional view 6B is taken. The arrow indicates the direction of sight.

Figure 6B:
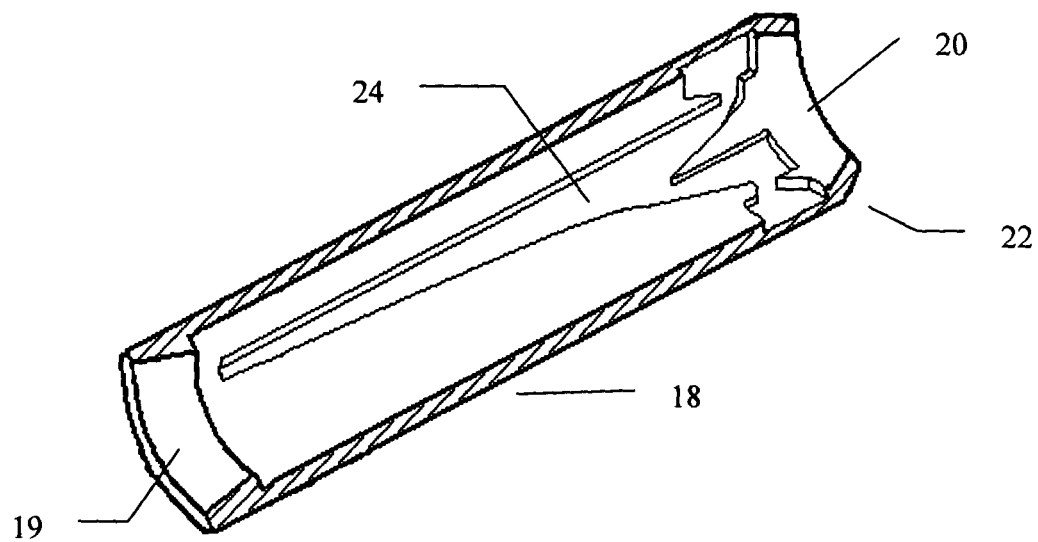

FIG. 6B shows the cross sectional view of the first shield portion of the needle safety cap device illustrating the groove configuration that locks and unlocks the device.

Figure 7A:
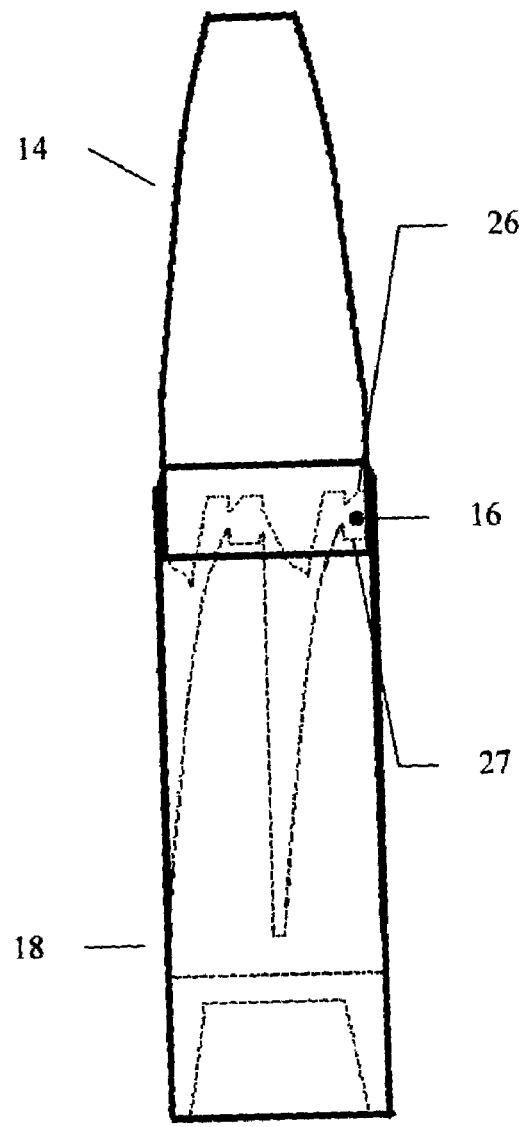

FIG. 7A shows the relationship between the knob and grooves of the needle safety cap device in the locked position.

Figure 7B:
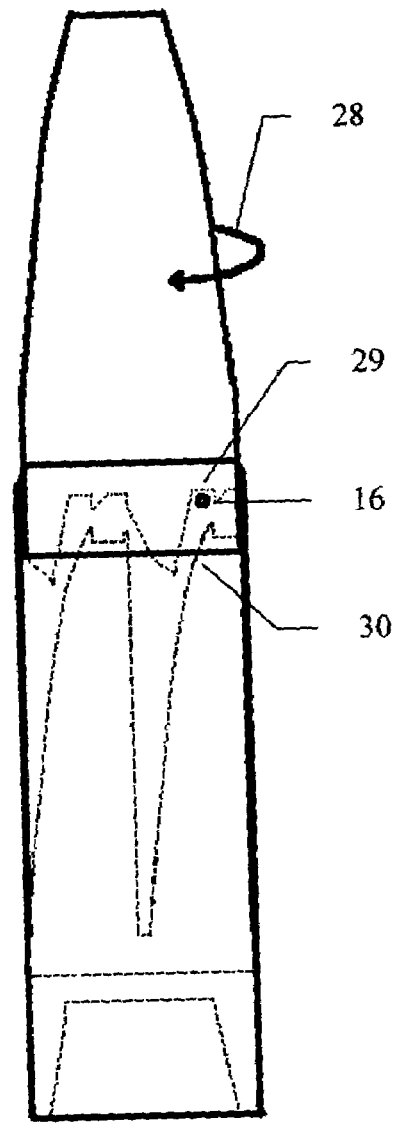

FIG. 7B shows the relationship between the knob and grooves of the needle safety cap device in the unlocked position.

Figure 7C:
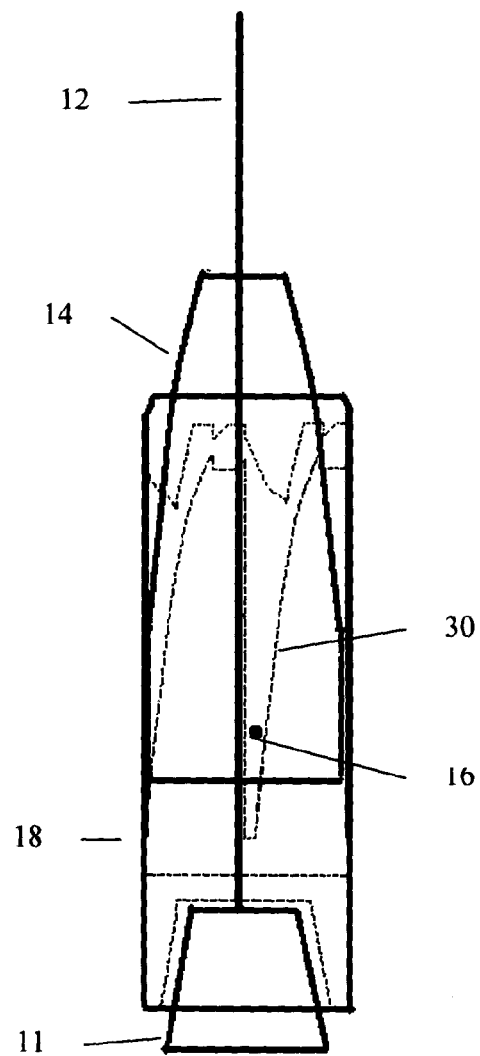

FIG. 7C shows the relationship between the knob and grooves of the needle safety cap device during injection.

Figure 7D:
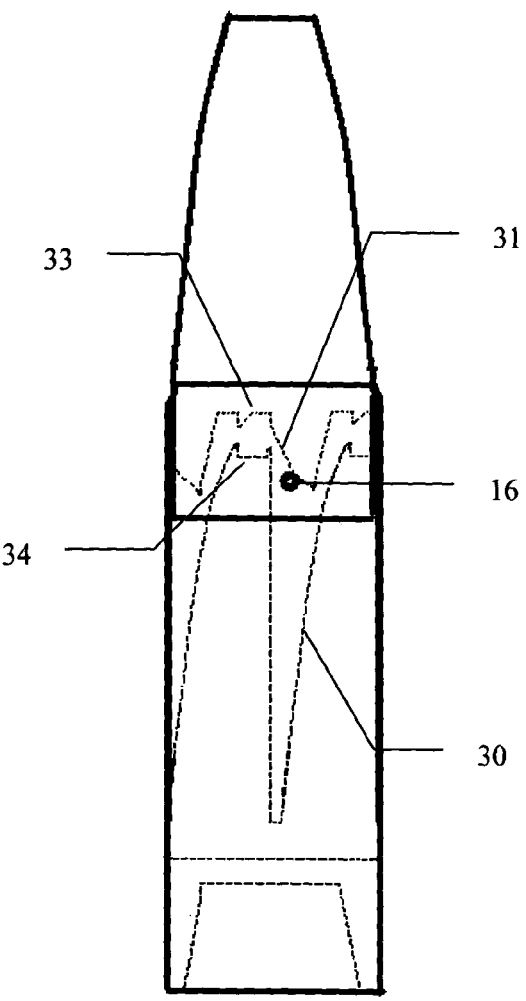

FIG. 7D shows the relationship between the knob and grooves of the needle safety cap device during needle withdrawal from tissue while being guided to a new locked position.

Figure 8A:
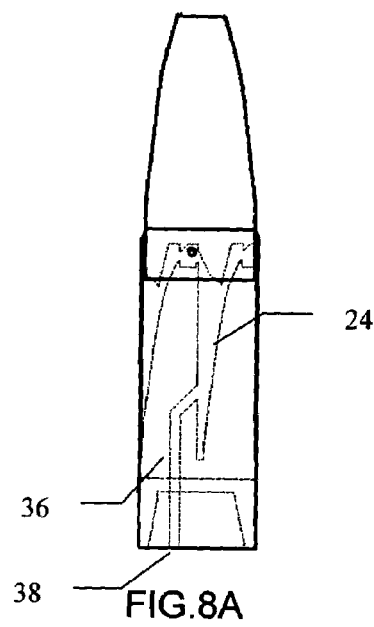

FIG. 8A shows a view of the accessory groove in the first shield portion of the needle safety cap device used for assembly of the second shield into the first shield.

Figure 8B:
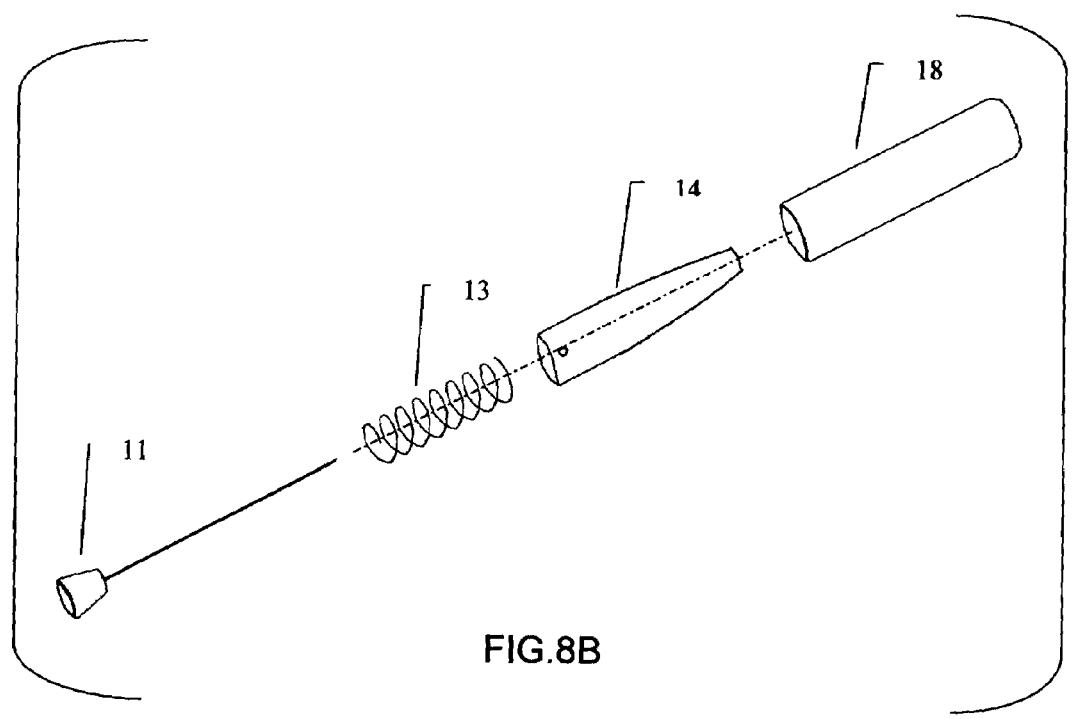

FIG. 8B is an exploded view showing the order of assembly of various parts of the needle safety cap device.

Figure 9:
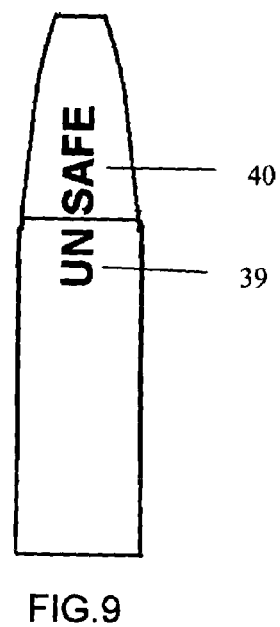

FIG. 9 shows an optional indicator that shows the status of the needle safety cap device as being safe or unsafe.

Figure 10:
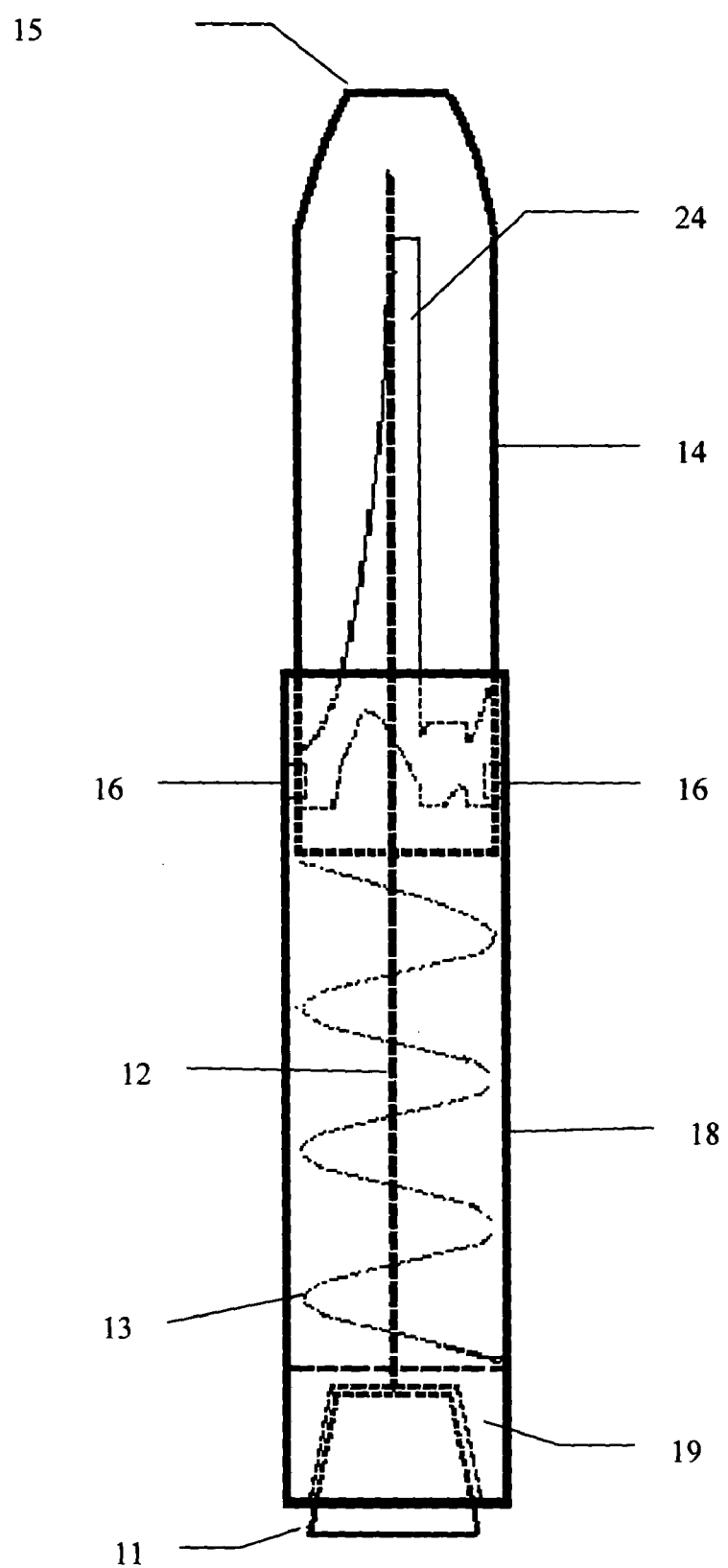

FIG. 10 shows an important ramification in design in which the guiding grooves are carved in the external portion of the second shield device and the knobs are placed inside the first shield of the device.

DRAWINGS—LIST OF REFERENCE NUMERALS 11. needle hub
12. needle
13. spring
14. second shield
15. opening for needle
16. knobs
18. first shield
19. opening where needle hub is inserted
20. opening where second shield passes thorough first shield
22. constriction
24. guiding grooves
26. wall restricting the knob from moving up in locked position
27. wall restricting the knob from moving down in locked position
28. arrow showing direction of twist to unlock
29. wall restricting the knob from moving up in unlocked position
30. guiding groove directing the knob toward left during injection 31. guiding groove directing the knob toward left after injection to new locked position
33. wall restricting the knob from moving up in new locked position
34. wall restricting the knob from moving down in new locked position
36. accessory groove used during assembly of second shield into the first shield
38. opening into groove where knob is inserted
39. "un" label
40. "safe" label

DETAILED DESCRIPTION—FIGS. 1 THROUGH 9—PREFERRRED EMBODIMENT

Figure 1:
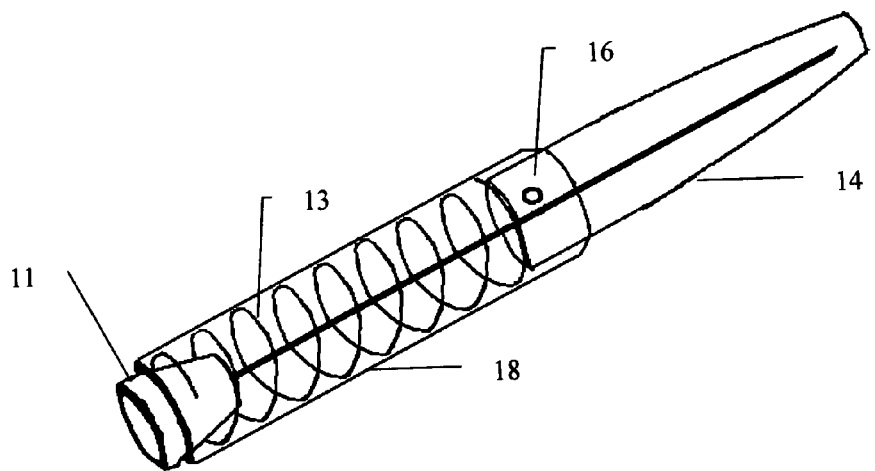
FIG. 1 is a perspective view of the needle safety cap device illustrating the location of the needle and the spring within the device.
Figure 2:
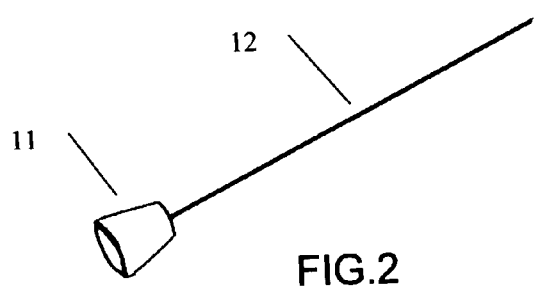
FIG. 2 is a perspective view of the needle and needle hub.
Figure 3:
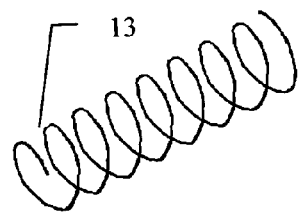
FIG. 3 is a perspective view of the spring.
Figure 4:
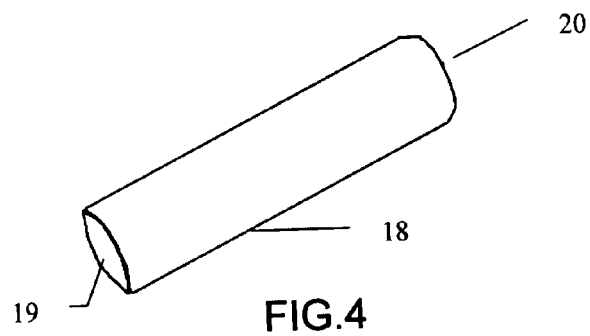
FIG. 4 shows a view of the first shield portion of the needle safety cap device.
Figure 5:
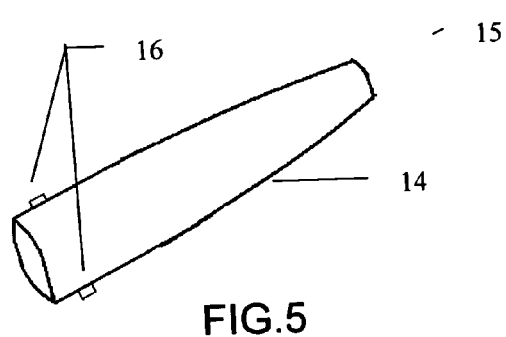
FIG. 5 shows a view of the second shield portion of the needle safety cap device.

As shown in FIGS. 1, 2 and 3, the present invention comprises a first shield 18, a second shield 14, a spring 13, a needle 12, and a needle hub 11. FIG. 1 shows a perspective view of the before mentioned parts of the assembled needle safety cap device. In the preferred embodiment, the first shield 18 and second shield 14 are a plastic material. FIG. 4 illustrates the two ends of the first shield 18. End 19 is where the standard needle hub is inserted, and end 20 is where the second shield 14 passes. FIG. 5 illustrates the second shield 14 with its opening 15 for the needle as well as the knob 16 which is used both for assembly of the needle safety cap device and function of the locking mechanism within the needle safety cap device.

FIGS. 6A and 6B illustrate the internal locking mechanism of the first shield 18. The guiding grooves 24 of this system are indicated as well as the area 19 where the standard needle hub fits with precision. FIG. 6B also illustrates the constriction 22 of the first shield 18.

FIG. 7A illustrates knob 16 of second shield 14 within the guiding grooves 24 of first shield 18 while in the locked position. Wall 26 within the groove system prevents knob 16 from moving upward while in the locked position. Wall 27 within the groove system prevents knob 16 from moving downward while in the locked position. FIG. 7B illustrates the knob 16 of the second shield 14 within the guiding grooves 24 of the first shield 18 while in the unlocked position. Twist 28 indicates the direction of movement of second shield 14, which moves knob 16 out of the locked position. Wall 29 within the groove system prevents knob 16 from moving upward in the unlocked position. Wall 30 directs knob 16 toward the left during injection. As shown in FIG. 7D, wall 31 directs knob 16 into another locked position. Wall 33 of the new locked position prevents knob 16 from moving upward, while wall 34 prevents downward movement of knob 16. The needle 12 and spring 13 are not shown in FIGS. 7A, 7B, and 7D, while the needle 12 is shown in FIG. 7C.

FIG. 8A illustrates the accessory groove 36 in the base of first shield 18 along with the opening 38. During assembly of the needle safety cap device, knob 16 of second shield 14 is inserted into opening 38 and guided into the groove system 24 by way of accessory groove 36. FIG. 8B illustrates the order of assembly of the parts of the needle safety cap device. The needle 12 and hub 11 are inserted into spring 13, which is then placed into second shield 14, and finally inserted into the accessory groove 36 of first shield 18. In other embodiments, the needle hub 11 can be affixed to first shield 18 with adhesive. Alternatively, the needle safety cap device can be assembled without needle 12 and hub 11.

FIG. 9 illustrates the indicator system of the needle safety cap device. In the preferred embodiment, the "Safe" label 40 is placed on second shield 14, while the "un" label 39 is placed on first shield 18. The two labels are aligned when the needle safety cap device is in the unlocked position. In other embodiments, there may be different indicators to illustrate the same point. For example, alignment of two dots can indicate that the locking mechanism is in effect.

FIG. 10—ADDITIONAL EMBODIMENTS

Additional embodiments are shown in FIG. 10. In this case, groove system 24 is carved on the external surface of second shield 14, while knob 16 is incorporated into the internal surface of first shield 18. The same system of operation is employed.

Operation—FIGS. 1 THROUGH 9

This simple needle cap can significantly reduce the number of accidental needle stick injuries for needles used in clinical situations, for example, attached to hypodermic syringes and catheters. This needle safety cap device covers the needle both before and after the injection. Before the injection, the second shield 14 is twisted, which unlocks the mechanism allowing second shield 14 to retract into first shield 18 during the injection. As the needle is removed from the tissue, second shield 14 again covers the needle and automatically locks. If second shield 14 is pressed downward while the device is in the locked position, second shield 14 will not retract and the needle will not become exposed. This automatic lock will prevent accidental needle sticks before and after injections. If another injection is needed, the second shield 14 is simply twisted again to unlock.

The invention differs from known devices for the same purpose in a number of ways. It is a passive system, which unlike most other needle safety devices automatically locks the cap on the needle rather than requiring the user to lock the cap on the needle. The invention modifies the cap only, and can be fitted on the full range of medical equipment using needles. Other devices for the same purpose modify the entire piece of equipment, for example the entire hypodermic syringe or the entire catheter. The device is easy to manufacture. It is made of two plastic parts and one spring, and it is easy to assemble.

As shown in FIG. 1, the invention comprises a first shield 18, a second shield 14, and a spring 13. In the preferred embodiment, the second shield 14 is conical in shape, with the narrower end closest to the needle tip to allow better visualization of the injection site. The spring 13 holds the second shield 14 in position completely shielding the needle and the second shield 14 can retract into the first shield 18 when the spring 13 is compressed, exposing the needle. The role of the spring 13 is to push the second shield 14 out of the first shield 18 to cover the needle and to push the locking mechanism into place. The device mounts onto the hub 11 holding the needle 12 to a medical device such as a syringe. The first shield 18 is designed to fit the standard needle hub which will attach to the standard syringe, eliminating the need for a different needle or syringe system.

FIGS. 7A, 7B, 7C, and 7D illustrate the operation of the present invention. In the locked position (FIG. 7A), the knob 16 of second shield 14 is between walls 26 and 27 of the groove system on the internal surface of first shield 18. At this point, if the second shield 14 is pressed downward, it will not retract and the needle will not be exposed. This is due to knob 16 contacting wall 27 in the locked position. Alternatively, if second shield 14 is pulled upward it will not disconnect from the device because knob 16 will contact wall 26 preventing second shield 14 from being removed.

Unlocking of the needle safety cap device is shown in FIG. 7B. The user simply twists second shield 14 which moves the knob 16 out of the locked position. At this point, if second shield 14 is pressed it will retract into first shield 18 exposing the needle for injection. While this occurs, knob 16 is being guided downward and to the left by groove 30. As the needle is being removed from the tissue (FIG. 7D), knob 16 is being moved toward the new locked position by groove 31. Once the injection is complete, the needle is completely covered and knob 16 is in the new locked position restricted now from upward or downward movement by walls 33 and 34 respectively. At this point, second shield 14 can no longer be retracted exposing the needle, unless the user manually unlocks the device again. The hub can be removed from the syringe system and the whole needle safety cap device can be disposed of without the possibility of accidental needle stick injury.

CONCLUSION, RAMIFICATIONS, AND SCOPE OF INVENTION

Thus the reader will see that the needle safety device of the invention provides a passive mechanism of action that can easily be attached to the hub of any standard needle without modifying the syringe system. The health care professionals can use the same standard syringe with the addition of this safety cap without altering their technique. The device can be used easily by the health care professional without the possibility of operator error. Also, the device can be unlocked if additional injections are necessary. The locking mechanism is incorporated into the cap which can easily be manufactured. No other needle safety device contains this locking mechanism, which is both simple and effective. In addition, this needle safety device meets all of the suggested criteria and directives of OSHA and the FDA.

While my above description contains many specificities, these should not be construed as limitations on the scope of the invention, but rather as an exemplification of one preferred embodiment thereof. Many other variations are possible. For example, there can be any number of retractable shields if needed to expose more length of the needle. Also, the cap can be manufactured without the needle. In this case there would need to be an additional piece of plastic at the base of the first shield to hold the spring. Another ramification would be to attach the needle with adhesive to the base of the first shield instead of the precision fit of the preferred embodiment. Additionally, a permeable barrier can be added at the end of the second shield nearest the end of the needle. This would be to ensure the sterility of the needle. Also, the shape of the shields can differ from the cylindrical shape, for example the shields can be conical. As mentioned previously, there can be any number of ways to indicate when the device is locked or unlocked. For example, red dots align when the device is in the locked position. The most important ramification is the possibility of having the groove system on the outer surface of the second shield, and the knobs on the inner surface of the first shield. This may be more efficient to manufacture.

Accordingly, the scope of the invention should be determined not by the embodiments illustrated, but by the appended claims and their legal equivalents.

What is claimed:

1. A retractable needle safety cap device comprising:
 a) a first shield having a first end and a second end with said first end having means of attachment to a needle hub,
 b) a second shield having a first end and a second end with said first end being telescopically mounted relative to said first shield and slideably moveable from an extended position covering a needle to a retracted position uncovering said needle when a force is applied to said second end of said second shield,
 c) a groove system formed on the inner surface of said first shield comprised of a continuous groove with guiding walls and restricting walls,
 d) a knob projecting from the outer surface of said first end of said second shield and being engaged to said groove system of said first shield and automatically guided into a locked position by said guiding walls upon extension of said second shield whereupon said restricting walls prevent further movement of said knob,
 e) a spring urging said second shield toward its extended position.

2. A retractable needle safety cap device as described in claim 1 wherein said groove system included a groove along the length of said first shield with a sloped guiding wall that directs said knob toward said first end of said first shield thereby retracting said second shield and exposing said needle while causing said second shield to rotate unidirectionally.

3. A retractable needle safety cap device as described in claim 2 wherein said groove system includes a sloped guiding wall which said knob will be guided against upon extension of said second shield whereby said knob will be urged into a locked position.

4. A retractable needle safety cap device as described in claim 3 wherein said restricting walls are oriented to prevent movement of said knob toward said second end of said first shield, toward said first end of said first shield, or rotational movement, and to maintain the locked position thereby preventing retraction of said second shield even with repeated pressure placed on said second end of said second shield.

5. A retractable needle safety cap device as described in claim 4 wherein said restricting walls are oriented to facilitate manual unlocking of said second shield by twisting thereby moving said knob into the unlocked position prior to injection.

6. A retractable needle safety cap device as described in claim 1 wherein said means of attachment of said first end of said first shield to said needle hub is precision fit attachment.

7. A retractable needle safety cap device as described in claim 5 wherein the uninterrupted circumferential design of said continuous groove permits an unlimited number of injections.

* * * * *